United States Patent [19]

Woodbury et al.

[11] Patent Number: 5,391,820

[45] Date of Patent: Feb. 21, 1995

[54] PREPARATION OF 3-MERCAPTOPROPIONITRILE AND 3-MERCAPTOPROPIONIC ACID

[75] Inventors: Richard P. Woodbury, Amherst; F. David Wood, Epson, both of N.H.

[73] Assignee: Hampshire Chemical Corp., Lexington, Mass.

[21] Appl. No.: 227,054

[22] Filed: Apr. 13, 1994

[51] Int. Cl.$^6$ .................................. C07C 148/00
[52] U.S. Cl. ................................... 562/512; 560/147
[58] Field of Search ................ 562/512, 147, 154; 528/279

[56] References Cited

U.S. PATENT DOCUMENTS

| | | | |
|---|---|---|---|
| 3,927,085 | 12/1975 | Zengel et al. | 260/526 S |
| 4,052,440 | 10/1977 | Gladstone et al. | 560/154 |
| 4,067,901 | 1/1978 | Gladstone et al. | 560/147 |
| 4,307,225 | 12/1981 | Louthan | 528/279 |
| 5,157,147 | 10/1992 | Chisholm et al. | 560/147 |
| 5,256,818 | 10/1993 | Tomioka | 562/512 |

FOREIGN PATENT DOCUMENTS 63-6545  1/1988  Japan .
58-198460 11/1988 Japan .
2082174  3/1982  United Kingdom .

*Primary Examiner*—Arthur C. Prescott
*Attorney, Agent, or Firm*—Nields & Lemack

[57] ABSTRACT

Facile process for the production of 3-mercaptopropionitrile and 3-mercaptopropionic acid by reacting thiodipropionitrile with alkaline hydrosulfide in the presence of alkaline hydroxide. Acidification of the resulting reaction product with a strong acid, or saponification, yields the desired mercaptopropionic acid, which can be isolated in high yield.

10 Claims, No Drawings

PREPARATION OF 3-MERCAPTOPROPIONITRILE AND 3-MERCAPTOPROPIONIC ACID

BACKGROUND OF THE INVENTION

β-mercaptopropionic acid is a suitable crosslinking agent for acrylic ester polymer, a suitable hardening agent for epoxy resin, and is used in synthetic resins for lenses, etc.

U.S. Pat. No. 5,256,818 to Tomioka discloses a method for making β-mercaptopropionic acid ($HSCH_2XH_2COOH$) by reacting alkaline thiodipropionate obtained from solid thiodipropionic acid, with alkaline sulfide. Specifically, sodium or potassium hydroxide is used to convert solid thiodipropionic acid to the corresponding thiodipropionate, which in turn is reacted with sodium sulfide at a temperature of 110° to 130° C. for one or several hours, preferably in the presence of residual alkaline hydroxide. The resulting solution is acidified with a strong acid to form the β-mercaptopropionic acid.

In an alternative embodiment disclosed in U.S. Pat. No. '818, the starting material is acrylonitrile, which is reacted with an excess of alkaline hydrosulfide or sulfide. Alkaline hydroxide is added, and alkaline β-mercaptopropionate is formed. Acidification with a strong acid yields β-mercaptopropionic acid, with alkaline sulfate is a by-product.

However, each of these methods requires relatively rigorous reaction conditions to convert the thiodipropionic acid to 3-mercaptopropionate. Such conditions can create problems with the composition of the product as well as the undesirable formation of by-products.

It therefore would be highly desirable to prepare 3-mercaptopropionic acid more efficiently, at lower reaction temperatures and with shorter reaction times.

SUMMARY OF THE INVENTION

The problems of the prior art have been solved by the present invention, which provides a facile process for the production of 3mercaptopropionitrile and 3-mercaptopropionic acid. In general terms, the process of the present invention utilizes thiodipropionitrile as the starting material, which is reacted with alkaline hydrosulfide in the presence of alkaline hydroxide to produce 3-mercaptopropionitrile in high yield. Acidification of the resulting nitrile with a strong acid, or saponification thereof, yields the desired mercaptopropionic acid in high yield.

DETAILED DESCRIPTION OF THE INVENTION

The present invention achieves production of high yields of 3-mercaptopropionitrile and 3-mercaptopropionic acid without contamination of dithiodipropionitrile and dithiodipropionic acid. Yield losses due to formation of sulfide derivatives, which are difficult to separate from the product, are avoided. In addition, isolation of thiodipropionitrile is avoided.

The present inventors have found that thiodipropionitrile will decompose in the presence of excess base and sodium hydrosulfide to form quantitative yields of 3-mercaptopropionitrile, which upon acidification yields 3-mercaptopropionic acid. This unexpected decomposition of thiodipropionitrile in the presence of excess base without the concomitant decomposition of the nitrile functionality allows for the subsequent formation of the acid. Although the present inventors are not to be limited thereby, the reaction mechanism for this decomposition is believed to be as follows:

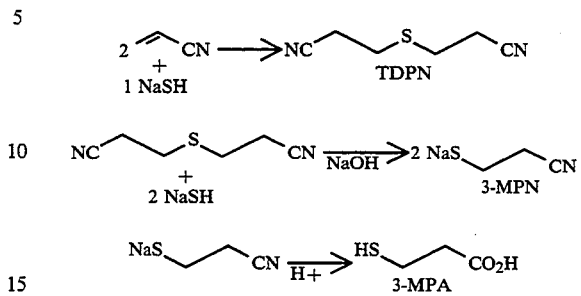

The conversion of the acrylonitrile and NaSH to 3-mercaptopropionitrile and thiodipropionitrile is based on the Michael Reaction, which involves the addition of a nucleophile (in this case, NaSH or the sodium salt of 3-mercaptopropionitrile) to an activated olefin (acrylonitrile). The salt of 3-mercaptopropionitrile is a better nucleophile than NaSH, and once formed, the nitrile will compete with the NaSH for the remaining acrylonitrile. These reactions are both extremely fast.

The thiodipropionitrile then undergoes a retro-Michael Reaction in the presence of sufficient base to remove the proton (hydrogen) on the carbon adjacent to one of the nitriles. This proton is relatively acidic in view of the strong electron withdrawing power of the nitrile:

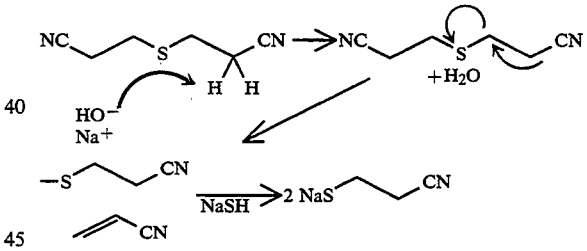

In accordance with the present invention, thiodipropionitrile is formed in near quantitative yield (about 96-98%) by reacting two moles of acrylonitrile with one mole of NaSH at a temperature of from about 35° C. to about 40° C., preferably about 40° C. Water can be added to the reaction medium. Preferably, the NaSH and the water are combined and heated to about 35° C., whereupon the acrylonitrile is rapidly added below the surface of the liquid while maintaining the temperature at about 40° C. Upon completion of the acrylonitrile addition (which should take about thirty minutes or less), the reaction mixture is stirred for an additional ten minutes.

The conversion of the thus formed thiodipropionitrile to 3-mercaptopropionitrile is accomplished by the addition of NaSH, preferably about 0.5702 moles, more preferably about 1.1 moles per mole of thiopropionitrile over a period of about ten minutes, allowing the reaction to exotherm to a temperature no higher than 60° C., preferably about 50°–60° C. The NaSH addition is followed by the rapid addition of base, preferably a tertiary amine such as triethanolamine, more preferably alkali metal hydroxide such as sodium or potassium hydroxide, most preferably sodium hydroxide, with little change in reaction temperature. The amount of 50% hydroxide to be added is preferably about 0.1–1 mole, more preferably about 0.5 moles per mole of thiopropionitrile. Alternatively, the base can be added first, followed by the gradual addition of NaSH.

Depending upon the amount of base used, the reaction mixture becomes clear within 5 to 60 minutes after the addition of NaSH is complete, which indicates that the reaction is complete. When using the above-stated preferred amounts of reactants, the reaction mixture becomes clear in about 13–15 minutes. The clear solution is then fed into an acidification/hydrolysis vessel while cooling the reaction vessel from 60° C. to room temperature.

The acid can be formed by acidification with a strong acid, preferably HCl or $H_2SO_4$. Hydrogen sulfide released is trapped with a caustic trap. Once the entire reaction mixture is acidified, the acid solution is refluxed for three hours. HCl concentration is preferably about 18% to 31.5%, most preferably about 27%. The higher concentrations results in the presence of solids during acidification. Even at the lower concentrations, solid formation can occur if the temperature falls below about 100° C.

The resulting 3-mercaptopropionic acid can be isolated by extraction with a solvent. Suitable solvents are fairly polar organic solvents in which the carboxylic functionality of the product are soluble, but which are immiscible with water. Examples of such solvents include methylisobutylketone, methylene chloride, methyl ethyl ketone and chloroform, with methylisobutylketone being preferred.

Alternatively, saponification can be used to form the acid from the nitrile. To that end, the solution of 3-mercaptopropionitrile, after the hold at 50°–60° C., is added over about a thirty minute period to a solution of sodium hydroxide (2.60 moles, 104 g) in water (416 g) at about 70° C. Upon completing the addition, the reaction mixture is heated slowly to a boil until the solution is ammonia free (about 2–3 hours). The solution is then acidified and extracted with a suitable organic solvent as above, and the 3mercaptopropionic acid is isolated via distillation.

The present invention will be more readily understood upon reference to the following non-limiting examples. Variations may be made by those skilled in the art without departing from the spirit and scope of the present invention.

EXAMPLE 1

A 500 ml. round bottom flask equipped with magnetic stirring and temperature control, was charged with 85.36 g (44%, 0.67 mole) of sodium hydrosulfide and 40.00 g of water. This solution was heated to 35° C. and 66.00 g (1.24 moles) of acrylonitrile was added below the surface of the reaction solution over a period of thirty minutes. The temperature of the reaction was kept below 40° C. during the addition of the acrylonitrile. The reaction mixture containing thiodipropionitrile was stirred for ten minutes, at 40° C., following the addition of the acrylonitrile.

The reaction mixture was heated to 45° C. and 165,89 g (44%, 1.30 moles) of sodium hydrosulfide was added as rapidly as possible, followed by the slow addition of 24.80 g (50%, 0.31 moles) of sodium hydroxide. The reaction exotherms during the addition of the sodium hydroxide and the temperature is maintained below 50° C. After the addition of the sodium hydroxide is complete, the reaction mixture is heated to 50°–60° C. for 30 minutes. After fifteen minutes, the heterogeneous mixture became homogeneous.

The reaction mixture was pumped directly into a acidification vessel containing 27% hydrochloric acid and refluxed for three hours. The aqueous solution contains a nearly quantitative yield of 3-mercaptopropionic acid. The 3-mercaptopropionic acid is isolated from the aqueous solution by extraction with methylisobutylketone followed by distillation.

EXAMPLE 2

The thiodipropionitrile (TDPN) was prepared as described in Example 1. The mixture containing TDPN was maintained at 40° C. during the addition of sodium hydrosulfide (165.89 g, 44%, 1.30 moles) and the sodium hydroxide (24.80 g, 50%, 0.31 moles). The temperature was maintained at 40° C. for three hours after the addition of the sodium hydroxide and then the reaction mixture was pumped directly into the acidification vessel and refluxed for three hours. The reaction mixture was not homogeneous prior to the acidification step. The yield of 3-mercaptopropionic acid was less than 80%, due to the low reaction temperature which did not allow the TDPN to decompose.

EXAMPLE 3

The thiodipropionitrile (TDPN) was prepared as described in Example 1. The mixture containing TDPN was maintained at 70° C. during the addition of sodium hydrosulfide (165.89 g, 44%, 1.30 moles) and the sodium hydroxide (24.80 g, 50% 0.31 moles). Following the addition of sodium hydroxide, the reaction mixture was heated at 70° C. for twenty minutes. The reaction became homogeneous after 10 minutes at 70° C. Following acidification as in Example 1, the aqueous solution contained 85% 3-mercaptopropionic acid, in view of the reaction temperature exceeding 60° C.

EXAMPLE 4

The thiodipropionitrile (TDPN) was prepared as described in Example 1. The reaction mixture containing TDPN was heated to 45° C. and 165.89 g (44%, 1.30 moles) of sodium hydrosulfide was added as rapidly as possible.

Instead of sodium hydroxide, an organic tertiary amine was added to catalyze the decomposition of TDPN. 9.25 g (0,062 moles) of triethanolamine was added slowly following the addition of the sodium hydrosulfide. After the addition of the triethanolamine was complete, the reaction mixture was heated at 60° C. for 30–150 minutes and then hydrolyzed. The time held at 60° C. had little effect on the final yield of 3-mercaptopropionic acid which ranged from 75–80% using this base.

What is claimed is:

1. A process for preparing 3-mercaptopropionic acid, comprising:
   a. reacting a molar excess of acrylonitrile with alkaline hydrosulfide to form thiodipropionitrile;
   b. reacting said thiodipropionitrile with alkaline hydrosulfide in the presence of base to form 3-mercaptopropionitrile; and
   c. acidifying the resultant nitrile with a strong acid.

2. The process of claim 1 wherein said alkaline hydrosulfide is sodium hydrosulfide.

3. The process of claim 1 wherein said base is selected from the group consisting of potassium hydroxide, sodium hydroxide and triethanolamine.

4. The process of claim 1 wherein said strong acid is HCl.

5. The process of claim 1, wherein said acrylonitrile is reacted with said alkaline hydrosulfide in a 2:1 molar excess.

6. A process for preparing 3-mercaptopropionitrile, comprising:
   a. reacting a molar excess of acrylonitrile with alkaline hydrosulfide to form thiodipropionitrile;
   b. reacting said thiodipropionitrile with alkaline hydrosulfide in the presence of base to form 3-mercaptopropionitrile.

7. The process of claim 6 wherein said alkaline hydrosulfide is sodium hydrosulfide.

8. The process of claim 6 wherein said base is selected from the group consisting of potassium hydroxide, sodium hydroxide and triethanolamine.

9. The process of claim 6, wherein said acrylonitrile is reacted with said alkaline hydrosulfide in a 2:1 molar excess.

10. The process of claim 6, further comprising saponifying the resulting 3-mercaptopropionitrile.

* * * * *